(12) United States Patent
Windolf et al.

(10) Patent No.: US 10,695,113 B2
(45) Date of Patent: Jun. 30, 2020

(54) BONE PLATE

(71) Applicant: AO Technology AG, Chur (CH)

(72) Inventors: Markus Windolf, Chermside (AU); Devakara Epari, Newstead West (AU); Michael Schuetz, St. Lucia (AU); Tim Pohlemann, Homburg-Saar (DE); Christoph Nötzli, Davos Platz (CH)

(73) Assignee: AO Technology AG, Chur (CH)

( * ) Notice: Subject to any disclaimer, the term of this patent is extended or adjusted under 35 U.S.C. 154(b) by 127 days.

(21) Appl. No.: 15/747,280

(22) PCT Filed: Aug. 7, 2015

(86) PCT No.: PCT/CH2015/000117
§ 371 (c)(1),
(2) Date: Jan. 24, 2018

(87) PCT Pub. No.: WO2017/024416
PCT Pub. Date: Feb. 16, 2017

(65) Prior Publication Data
US 2018/0206895 A1 Jul. 26, 2018

(51) Int. Cl.
*A61B 17/80* (2006.01)
(52) U.S. Cl.
CPC .......... *A61B 17/8085* (2013.01); *A61B 17/80* (2013.01); *A61B 17/8061* (2013.01); *A61B 17/8033* (2013.01)
(58) Field of Classification Search
CPC .................. A61B 17/8061; A61B 17/8085
See application file for complete search history.

(56) References Cited

U.S. PATENT DOCUMENTS 2,580,821 A * 1/1952 Toufick .............. A61B 17/8004
606/282
5,702,399 A * 12/1997 Kilpela .................. A61B 17/82
606/103
(Continued)

FOREIGN PATENT DOCUMENTS

EP 1221308 A1 7/2002
WO 03039384 A1 5/2003

*Primary Examiner* — Christian A Sevilla
(74) *Attorney, Agent, or Firm* — Rankin, Hill & Clark LLP

(57) ABSTRACT

The bone plate (1) has a lower surface (2), an upper surface (3), a thickness T measured between the lower and upper surfaces (2;3), a longitudinal axis (4) and a plurality of plate holes (5) running from the lower surface (2) to the upper surface (3). The bone plate (1) further has a slot (6) extending from the lower surface (2) towards the upper surface (3) and having a width W measured at the lower surface (2) and parallel to the longitudinal axis (4). The slot (6) extends to a maximum distance D measured from the lower surface (2) towards the upper surface (3) of 0.4-0.9 times the thickness T of the bone plate (1). The slot (6) has a width measured parallel to the longitudinal axis (4) which at its maximum extension E is at least 0.8 mm, preferably of at least 3 mm. The slot (6) allows the plate (1) to bend longitudinally—additionally to the intrinsic bendability of the unslotted plate (1)—at most to the amount of 20°, preferably at most to the amount of 10°. Due to the bi-phasic properties of the bone plate (1) optimal bending properties and adaptability to anatomical surfaces are achieved.

33 Claims, 16 Drawing Sheets

(56) References Cited

U.S. PATENT DOCUMENTS

| | | | |
|---|---|---|---|
| 5,718,705 A * | 2/1998 | Sammarco | A61B 17/8085 606/260 |
| 2010/0063505 A1 | 3/2010 | Frigg et al. | |
| 2012/0277748 A1 | 11/2012 | Trescony et al. | |
| 2014/0343350 A1 | 11/2014 | Martinson et al. | |
| 2015/0039033 A1 | 2/2015 | Biedermann | |

\* cited by examiner

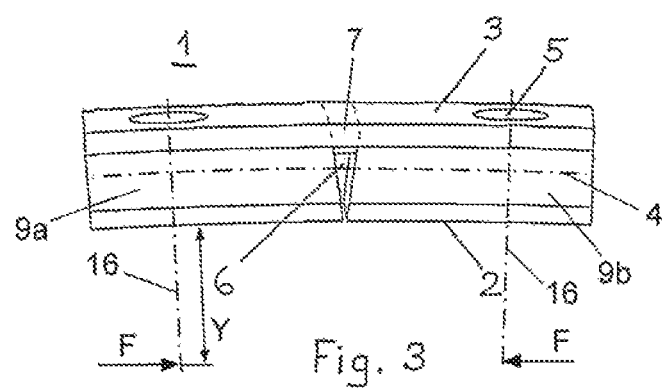

BONE PLATE

BACKGROUND OF THE INVENTION

1. Field of the Invention

The invention relates to a bone plate.

2. Description of the Related Art

From US 2012/0277748 Trescony et al. a bone plate is known which has a multitude of slots which allow the bone plate to bend in the longitudinal direction. The multitude of slotted structures sequentially arranged along a longitudinal axis provides maximum flexibility to the bone plate but leads to a decreased stability of the plate.

The problem to be solved can be seen in further development of such a bone plate which has only a relatively limited flexibility so as to achieve loose-lock stability of the bone plate.

BRIEF SUMMARY OF THE INVENTION

It is an object of the invention to provide a bone plate with bi-phasic properties with optimal bending properties and adaptability to anatomical surfaces.

The invention solves the posed problem with a bone plate as disclosed and claimed herein.

The slot in the bone plate according to the invention has the function to provide flexibility to a bone fracture for promotion of secondary bone healing even at low functional loading of the patient, and at the same time to limit the interfragmentary motion to a preferable range when the slot closes. Fracture stimulation becomes therefore widely independent from the magnitude of functional loading.

It was found that interfragmentary motion of 0.5 mm (0.2-1 mm) provides a good healing outcome in different fracture sizes (1, 2 and 6 mm cover the vast majority of fractures). The bone plate according to the invention with an optimized slot width avoids overstimulation of the fracture, which could lead to healing complications such as hypertrophic delayed- and non-unions. It has to be noted that technically, due to flexibility, compliance and geometrical arrangements of the bone-plate according to the invention the actual interfragmentary motion will be higher than the slot-width.

Some advantages of the bone plate according to the invention are the following:

The bone plate according to the invention exhibits a bi-phasic stiffness behavior. To promote secondary bone healing, the plate permits required interfragmentary motion at low functional loading (flexible phase), and limits said motion to a maximum when the slot closes at higher magnitudes of functional loading (rigid phase). The plate, hence, provides controlled motion to the bone fracture largely independent from the magnitude of functional loading. Thereby (i) healing complications caused by mechanically adverse conditions can be avoided and (ii) the average time to bony union may be shortened.

Conventional bone plates are limited in their size in terms of cross-sectional area, because excessive rigidity would impair bone healing processes. This, in turn, often leads to overloading of the plate material and implant failure. Surgeons tend to restrict patient weight bearing at the direct post-operative phase to avoid construct failure. However, scientific findings stress the importance of early weight bearing for fast and robust fracture healing. The plate according to the invention enables an increase in cross sectional area at the location of the highest material stress to strengthen the implant and consequently to allow full weight bearing of the patient. At the same time, it provides the required flexibility.

Plating of bone fractures frequently leads to healing complications close to the plate body. When the plate flexes, the mechanical stimulus gradually increases with the distance to the plate. Directly underneath the plate the generated motion is often too small to foster fracture healing. Opposed to conventional bone plates, the plate according to the invention provides mechanical stimulus at its direct proximity for avoiding mentioned healing complications.

Interfragmentary motion (IFM) of fractures fixed with conventional plates strongly depends on the screw configuration. Too short working length (distance between innermost screws bridging the fracture) can lead to under-stimulation whereas too long working length can result in overstimulation. The plating technique is therefore not trivial and requires experience of the surgeon. The bone plate according to the invention simplifies this procedure significantly, because IFM is essentially controlled by the geometry of the slot in the bone plate. As a result positions of bone screws become uncritical with regard to the flexibility of fixation.

Further advantageous embodiments of the invention can be commented as follows.

In a special embodiment the slot has a width W in the range of 0.1 to 1.3 mm, preferably in the range of 0.2 to 0.3 mm.

In a further embodiment the bone plate comprises a material section rigidly connected to an upper section of the bone plate adjacent to the upper surface of the bone plate extending to the lower surface and thereby crossing the slot; the material section sitting inside a cavity extending from the lower surface towards the upper surface and having a clearance C. The material section may be a bolt, preferably a circular-cylindrical bolt comprising one or more circular cylindrical sections and the cavity (17) may have a shape corresponding to the bolt, preferably comprising one or more circular-cylindrical sections. Manufacturing is simplified and more efficient when using a second element such as e.g. a bolt in a bore hole as motion limiter. Clearance and thereby maximum movement can be accurately adjusted by the diameters of hole and bolt. Under bending of the bone plate, the bolt acts as limiter of the plate deflection when contact between bolt and bore hole is achieved.

In a further embodiment the width W of the slot is larger than 0.20 mm, preferably larger than 0.25 mm. The width W of the slot may be smaller than 0.35 mm, preferably smaller than 0.30 mm. Most preferably the width W of the slot is in the range of 0.2 to 0.3 mm. The slot may exhibit a width W over a vertical height of minimum 2 mm, preferably minimum 3 mm measured vertically from the lower surface of the bone plate. In a further embodiment the lower surface of the bone plate is designed to contact a bone surface.

The thickness of the bone plate may be in the range of 6 mm-12 mm. Preferably the thickness is in the range of 8 mm-10 mm, preferably for use on the femur. Typically the thickness may be 9 mm.

In a further embodiment the thickness of the bone plate is in the range of 4 mm-7 mm preferably for use on the humerus or tibia. Typically the thickness of the plate for this application may be 6 mm.

In a further embodiment the bone plate has a width measured at the lower surface at the position of the slot and vertically to the longitudinal axis in the range of 14 mm-22 mm, preferably in the range of 17 mm to 21 mm. Typically the width may be 19 mm. By increasing the plate width the cross-sectional area is increased accordingly and leads to reduced stresses. The stress within a plate with the specified thickness and width made from standard implant materials such as stainless steel or Titanium alloys under functional loading of the patient will be in a range that full weight-bearing can be tolerated directly post-operative with the entire load borne by the plate. This enables the patient to immediately regain independency and functionality of the limb; it accelerates return to work and stimulates bone healing at an early stage.

In a further embodiment the slot allows the plate to bend longitudinally at least to the amount of 1.0°, preferably at least 1.5°.

In a further embodiment the slot allows the plate to bend longitudinally—additionally to the intrinsic bendability of the unslotted plate (1)—at most to the amount of 5°, preferably at most 4°.

Preferably the length of the lower surface is shortened at most 1 mm upon closure of the slot (6) at the lower surface (2) of the bone plate (1) so that the width W is equal to 0.

In a further embodiment a force in the range of 50-400 N, preferably in the range of 100-300 N, acting essentially parallel to the longitudinal axis of the plate with an offset of 10 mm to 30 mm from the lower surface of the bone plate is sufficient to close the slot at the lower surface of the bone plate so that the width W is equal to 0.

In a further embodiment the slot of the bone plate has the shape of an "L", the free end of the shorter leg of the "L" opening into the lower surface with a width W and the longer end of the "L" running essentially parallel to the longitudinal axis and having the length E.

In a further embodiment the slot of the bone plate has the shape of a "T" the free end of the vertical leg of the "T" opening into the lower surface with a width W and the two horizontal legs of the "T" running essentially parallel to the longitudinal axis and having the length E.

In a further embodiment the slot has a curved-shaped form seen in a longitudinal cross-section of the bone plate, the curved-shaped form enlarging from the lower surface towards the upper surface. This provides resistance against torsion and shearing when the slot closes.

In a further embodiment the slot has an Ω-shaped form seen in view on the lower surface of the bone plate, wherein the Ω-shaped form has an axis of symmetry extending in the direction of the longitudinal axis of the bone plate. This provides resistance against tension and valgus bending.

In a further embodiment the slot of the bone plate has
(i) a lower part essentially running in the direction of the plate thickness and which opens into the lower surface; and
(ii) an upper part essentially running parallel to the longitudinal axis and which is closed with respect to the upper surface.

In a further embodiment the plate thickness T and the plate width gradually decrease from the slot towards both ends of the plate. This acknowledges the fact that the most loaded area of the plate is at the position of the slot. This is where stability needs to be provided by adding material, whereas loading decreases towards the ends. The volume of the plate can thereby be minimized to reduce the effect on the biological surroundings.

In a further embodiment at least one of the plurality of plate holes is configured to receive an angular stable locking screw at a predefined angle. In another embodiment at least one of the plurality of plate holes is configured to receive a variable angle locking screw.

In a further embodiment the plate holes have different sizes to receive bone screws of different diameters. This offers the advantage to avoid screw breakage under high functional loading, larger diameter screws (e.g. 6 mm) could be particularly useful at positions close to the fracture (screw locations with the highest load exposure) whereas standard diameter screws (e.g. 5 mm) are sufficient more remote from the fracture.

In a further embodiment the 3D-shape of the plate is pre-shaped to a specific anatomical fit.

In a further embodiment the bone plate has two slots in a distance from each other measured longitudinally of more than 50 mm.

In a further embodiment the bone plate has a compartment extending from the lower surface of the plate towards the upper surface to accommodate one or more sensors, preferably for measuring strain or displacement or load or pressure or temperature.

In a further embodiment the bone plate has a compartment extending from the lower surface of the plate towards the upper surface to accommodate one or more actuators, to store drugs for controlled release, or to provide space for callus growth.

In a further embodiment the width W of the slot is essentially equal to the length E of the slot.

In a further embodiment the bone plate is configured in two-piece form, preferably in a region adjoining the slot. This configuration of the bone plate permits the advantage that by producing one contact face of the slot by a separate part assembled to the bone plate, slots with small slot width and complex geometry can be realized.

The bone plate can be made of stainless steel, titanium or a titanium alloy.

The bone plate according to the invention can be used for the treatment of bone fractures.

The invention regards also a method of manufacture of the bone plate according to the invention and which is characterized in that the slot of the bone plate is produced by cavity sinking EDM.

BRIEF DESCRIPTION OF THE DRAWINGS

Several embodiments of the invention will be described in the following by way of example and with reference to the accompanying drawings in which:

FIG. 3 illustrates a perspective view of the bone plate of FIG. 1 under stress so that the slot is closed;

DETAILED DESCRIPTION OF THE INVENTION

Figure 1:
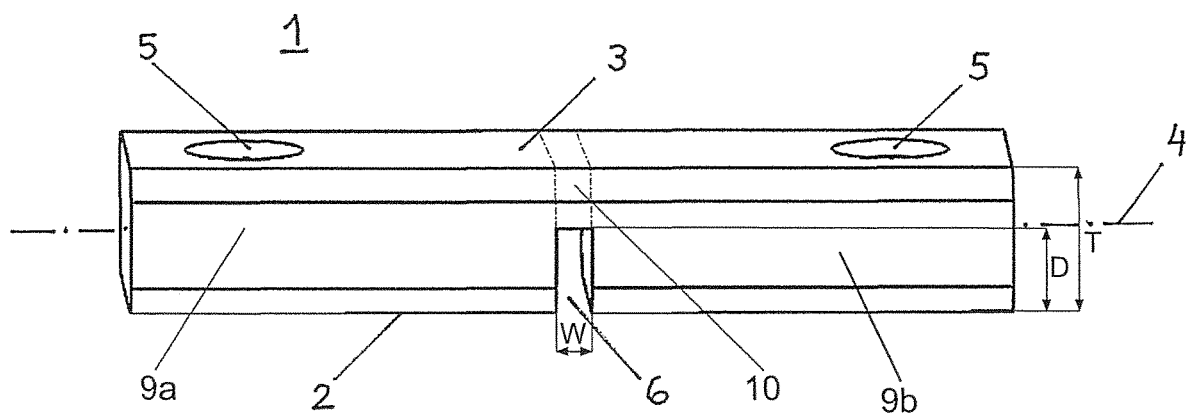
FIG. 1 illustrates a perspective view of an embodiment of the bone plate according to the invention
Figure 2A:
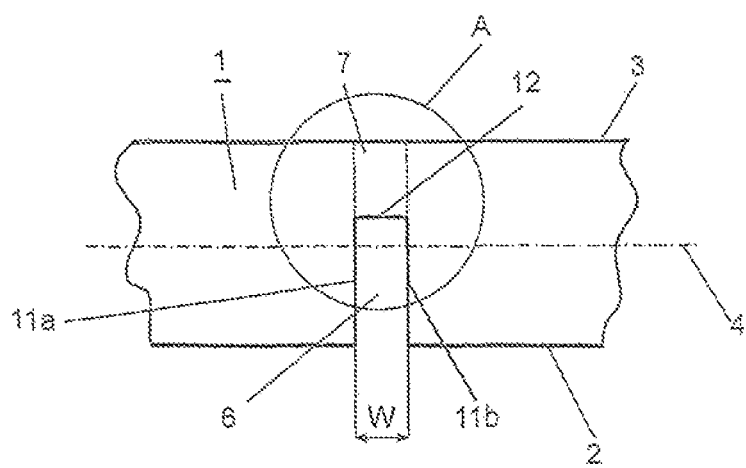
FIG. 2a illustrates a magnified longitudinal section through the bone plate of FIG. 1 in the region of the slot and in a stress-free state.

FIGS. 1-3 illustrate an embodiment of the bone plate 1 according to the invention which comprises a longitudinal axis 4, a lower surface 2 designed to contact a bone surface, an upper surface 3 and a plurality of plate holes 5 penetrating the bone plate 1 from the lower surface 2 to the upper surface 3. The bone plate 1 has a thickness T measured between the lower and upper surfaces 2;3 and includes at least one slot 6 extending from the lower surface 2 towards the upper surface 3 to a maximum distance D measured from the lower surface 2 towards the upper surface 3.

Exemplarily but not limiting, the slot 6 comprises two planar lateral sides 11a, 11b (FIG. 2a) arranged orthogonal to the longitudinal axis 4 and a planar top side 12 directed towards the upper surface 3 of the bone plate 1. The slot 6 is located in the longitudinal middle section of the bone plate 1 and has a maximum dimension D of about 0.4 to 0.9 times of the thickness T of the bone plate 1. Due to the slot 6 the flexural rigidity (also called bending stiffness) of the bone plate 1 is significantly reduced in the region of the slot 6 so that the bone plate 1 is divided into three longitudinal sections, namely a flexible section 10 in the region of the slot 6 and two rigid sections 9a, 9b whereof each one extends to one lateral end of the bone plate 1. The plate holes 5 are located in the rigid sections 9a, 9b so that bone fasteners (exemplarily indicated in FIG. 3 by their bone screw axes 16) extending through the plates holes 5 and fixed in bone fragments are arranged in the rigid sections 9a, 9b of the bone plate 1. Therefore, the load acting onto the bone plate 1 due to the weight of the patient or due to forces exerted by the patient is applied to the rigid sections 9a, 9b of the bone plate 1.

Depending on the shapes and sizes of the slot 6 and the bridging portion 7 a force F in the range of 50-400 N acting essentially parallel to the longitudinal axis 4 of the bone plate 1 with an offset Y of 10 mm to 30 mm from the lower surface 2 of the bone plate 1 is sufficient to close the slot 6 at the lower surface 2 of the bone plate 1 so that the width W at the lower surface 2 is equal to 0 (FIG. 3).

The slot 6 extends fully across the bone plate 1 with a constant width so that the width W measured at the lower surface 2 parallel to the longitudinal axis 4 of the bone plate 1 coincides with the maximum extension E of the slot 6. In the flexible section 10 the bone plate 1 is formed as a beam shaped bridging portion 7 (FIG. 2a) which is vertically limited by the top side 12 of the slot 6 and the upper surface 3 of the bone plate 1. In the direction of the longitudinal axis 4 the bridging portion 7 extends over the maximum extension E of the slot 6 which—in the embodiment of FIGS. 1 to 3—coincides with the width W of the slot 6.

Due to the reduced flexural rigidity of the bridging portion 7 compared to the rigid sections 9a,9b of the bone plate 1 the bone plate 1 bends first in the flexible section 10. Under a bending load applied in this manner compressive and tensile forces develop in the direction of the longitudinal axis 4 which induce stresses on the bone plate 1. If the effect of the bending moment resulting from applied bending load tends to close the slot 6 the maximum compressive stress is found at the top side 12 of the slot 6 while the maximum tensile stress is found at the upper surface 3. Between the two sections with opposing stresses there is the neutral axis 8 (FIG. 2b) where there is no bending stress.

Figure 2B:
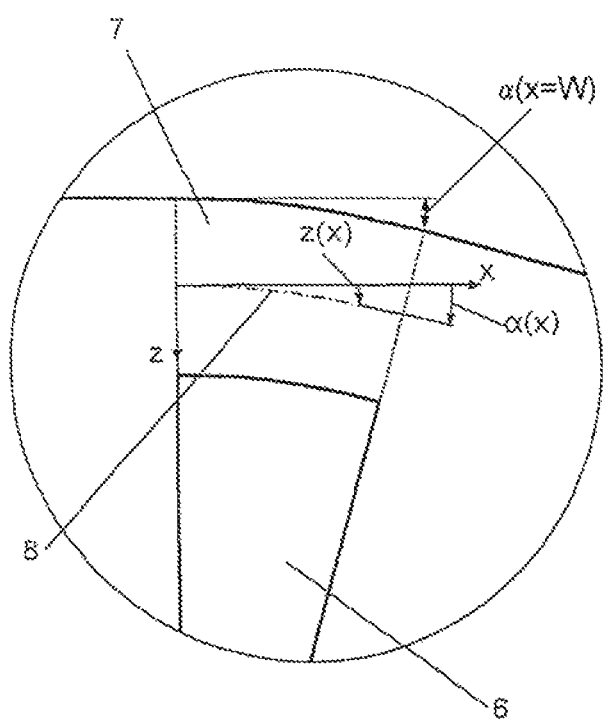
FIG. 2b illustrates a magnified view of detail A in FIG. 2a when the bone plate is bent.

According to the Euler-Bernoulli bending theory the curvature of the neutral axis 8 is proportional to the bending moment and inversely proportional to the flexural rigidity (bending stiffness), wherein the flexural rigidity is defined as the product E*I, where E is the elastic modulus or also called Young's modulus and I is the second moment of area of the cross-section of the bridging portion 7. For small deflections of the neutral axis 8 the curvature is considered as the second derivative of the deflection z of the neutral axis 8 at a position x (FIG. 2b). The curve z(x) describes the deflection of the neutral axis 7 in the z direction at some position x. The angle of inclination a(x) of the neutral axis 8 which is the first integral of the curvature as well as the deflection z(x) are therefore additionally dependent on the length of the structure, i.e. dependent on the width of the slot 6. When the bone plate 1 bends under a load applied onto the upper surface 3 essentially orthogonal to the longitudinal axis 4 the slot 6 becomes narrower and finally closes (FIG. 3). For the narrowing and the closure of the slot 6 the deflection z(x=W) of the bridging portion 7 is relevant only, while an eventual bending deformation of the rigid sections 9a,9b of the bone plate 1 can be neglected.

The transition from the flexible phase to the rigid phase of the bone plate 1 occurs when the slot 6 closes and therefore depends on the deflection z(x=W) of the bridging portion 7 which is as described above a function of the bending moment, the flexural rigidity of the bridging portion 7 and the length thereof measured in the direction of the longitudinal axis 4 of the bone plate 1. The deflection z(x=W) which is reached when the slot 6 closes then determines the allowed motion of the bone fragments.

As describe above the flexural rigidity (also called bending stiffness) of the bone plate 1 is significantly reduced in the region of the slot 6 so that the bone plate 1 is divided into three longitudinal sections, namely a flexible section 10 in the region of the slot 6 and two rigid sections 9a, 9b whereof each one extends to one lateral end of the bone plate 1. In the flexible section 10 the bone plate 1 is formed as a beam shaped bridging portion 7 (FIG. 2a) which is vertically limited by the top side 12 of the slot 6 and the upper surface 3 of the bone plate 1. In the direction of the longitudinal axis 4 the bridging portion 7 extends over the maximum extension E of the slot 6 which—in the embodiment of FIGS. 1 to 3—coincides with the width W of the slot 6 measured at the lower surface 2 of the bone plate 1 parallel to the longitudinal axis 4. Due to the reduced flexural rigidity of the bridging portion 7 compared to the rigid sections 9a, 9b of the bone plate 1 the bone plate 1 bends first in the flexible section 10, while an eventual bending deformation of the rigid sections 9a, 9b of the bone plate 1 can be neglected. The bending angle of the bone plate 1 therefore coincides with the angle of inclination a(x=W) of the bridging portion 7 (FIG. 2b) that can be measured at the upper surface 3 of the bone plate 1 as the angle between the tangents at the borderlines of the bridging portion 7.

However, the maximum allowable deflection z(x=W) is dependent on the maximum stress induced by the bending moment, i.e. the maximum tensile stress at the upper surface 3 of the bone plate 1 or the maximum compressive stress at the top side 12 of the slot 6. Therefore, another limitation of the allowable deflection z(x=W) is that the maximum stress occurring in the bridging portion 7 of the bone plate 1 may not exceed the yield stress of bone plate material.

Figure 14:
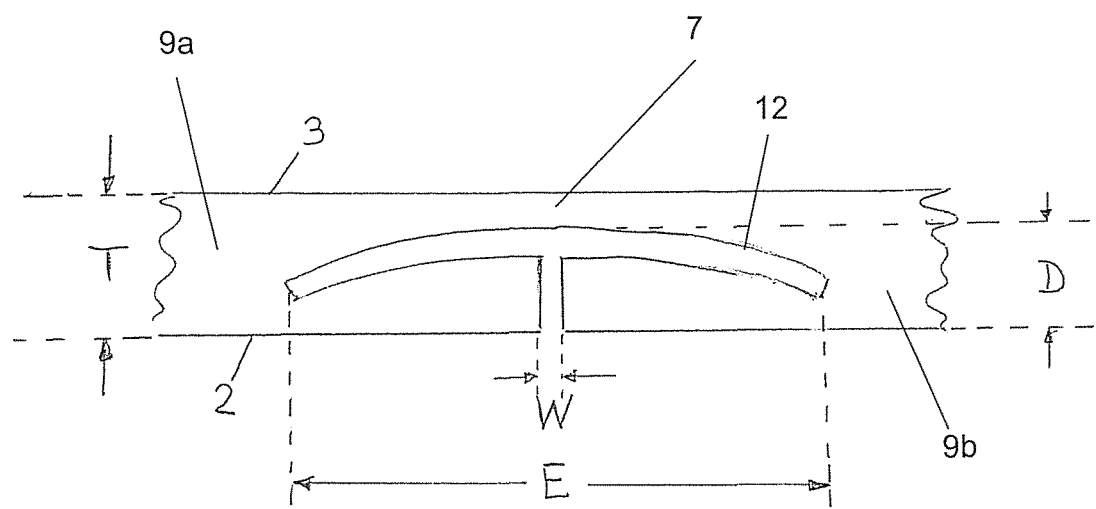
FIG. 14 illustrates a side view of a portion of the bone plate according to a further embodiment.
Figure 15A:
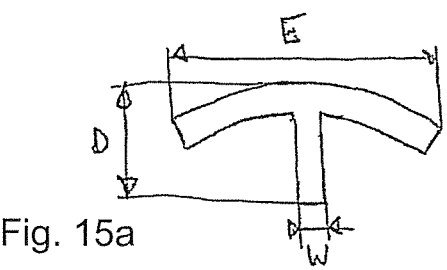
FIGS. 15a-e schematically illustrate slot profiles of further embodiments of the bone plate according to the invention.

As illustrated in FIGS. 14 and 15a the slot 6 can be configured with the shape of a "T" wherein the free end of the vertical leg of the "T" opens into the lower surface 2 with the width W and the two horizontal legs of the "T" are curved and extend in the direction of the longitudinal axis 4 of the bone plate 1 to a maximum extension E of the width of the slot 6 measured parallel to the longitudinal axis 4.

The top side 12 of the slot 6 extends along the two horizontal legs of the "T" so that the length of the bridging portion 7 in this case corresponds to the maximum extension E. Because the deflection z(x=E) of the bridging portion 7 depends on a higher degree on the length of the bridging portion 7 than the stress induced on the bridging portion 7 via the bending moment the configuration of the flexible section of the bone plate 1 can be optimized with respect to the desired deflection required for closing the slot 6 and with respect to the maximum stress occurring in the bridging portion 7. Furthermore, due the curved configuration of the two horizontal legs of the "T" the height of the bridging portion 7 measured between the top side 12 of the slot 6 and the upper surface 3 of the bone plate 1 varies along the length of the bridging portion 7 from a minimum height in the longitudinal middle plane of the bridging portion 7 to a maximum at the change-over from the bridging portion 7 to the rigid sections 9a, 9b of the bone plate 1. The flexural rigidity of the bridging portion 7 at a position x is dependent on the height of the bridging portion 7 at the position x so that the bridging portion 7 can be configured with a varying flexural rigidity where the variation of the flexural rigidity can be specifically adapted to optimize the stress distribution in the bridging portion 7.

Figure 15B:
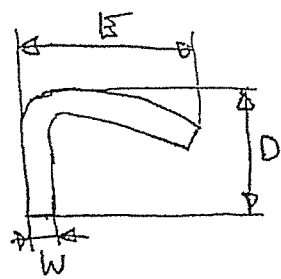
Figure 15C:
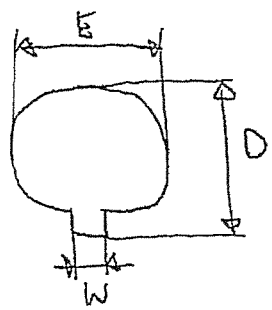
Figure 15D:
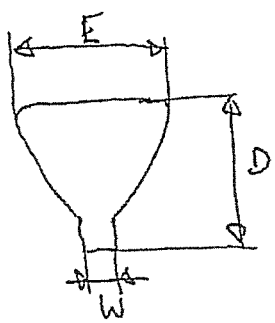
Figure 15E:
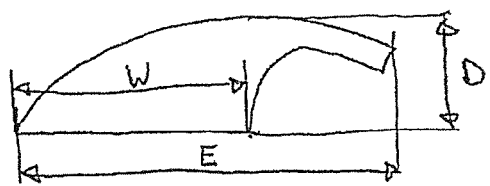

A similar effect can be achieved by a configuration of the slot 6 with the shape of an "L" where the free end of the shorter leg of the "L" opens into the lower surface 2 with a width W and the longer leg of the "L" extends essentially parallel to the longitudinal axis 4 and provides the maximum extension E of the width of the slot 6 (FIGS. 15b and 15e).

The configuration of the slot 6 illustrated in FIG. 15c permits an optimization of the stress distribution in the bridging portion 7 due to the specific variation of the flexural rigidity together with an optimization of the flexible section of the bone plate 1 with respect to the desired deflection required for closing the slot 6 and with respect to the maximum stress occurring in the bridging portion 7 as described above.

The configuration of the slot 6 illustrated in FIG. 15d permits an optimization of the flexible section of the bone plate 1 with respect to the desired deflection required for closing the slot 6 and with respect to the maximum stress occurring in the bridging portion 7 as described above. The slot 6 has a curved-shaped form seen in a longitudinal section of the bone plate 1 wherein the curved-shaped form enlarges from the lower surface 2 towards the upper surface 3. Furthermore, due to the rounded edges limiting the slot 6 at its maximum extension E peak stresses due to sharp edges can be avoided.

Depending on the required deflection of the bridging portion 7 and with consideration of the allowed maximum stress induced in the bridging portion 7 by means the load applied preferred sizes of the slot 6 can be as follows:

the width W measured at the lower surface 2 and parallel to the longitudinal axis 4 can be in the range of 0.1 to 1 mm, preferably in the range of 0.2 to 0.3 mm; and the vertical height of the slot is minimum 2 mm measured vertically from the lower surface 2 of the bone plate 1.

The above dimensions of the slot 6 permit an angle of inclination $\alpha$ (x=E) of at least 1.0°, preferably at least 1.5° so as to limit the bending angle of the bone plate 1 to maximum 5°, preferably maximum 4° excluding the intrinsic bendability of the unslotted plate 1. Furthermore, the bending angle of the bone plate 1 can be limited so that the length of the lower surface 2 at most 1 mm upon closure of the slot 6 at the lower surface 2 of the bone plate 1. A force in the range of 50-400 N, preferably in the range of 100-300 N which acts essentially parallel to the longitudinal axis 4 of the bone plate 1 and which has an offset of 10 mm to 30 mm from the lower surface 2 of the bone plate 1 is sufficient to close the slot 6 at the lower surface 2 of the bone plate 1.

Figure 4:
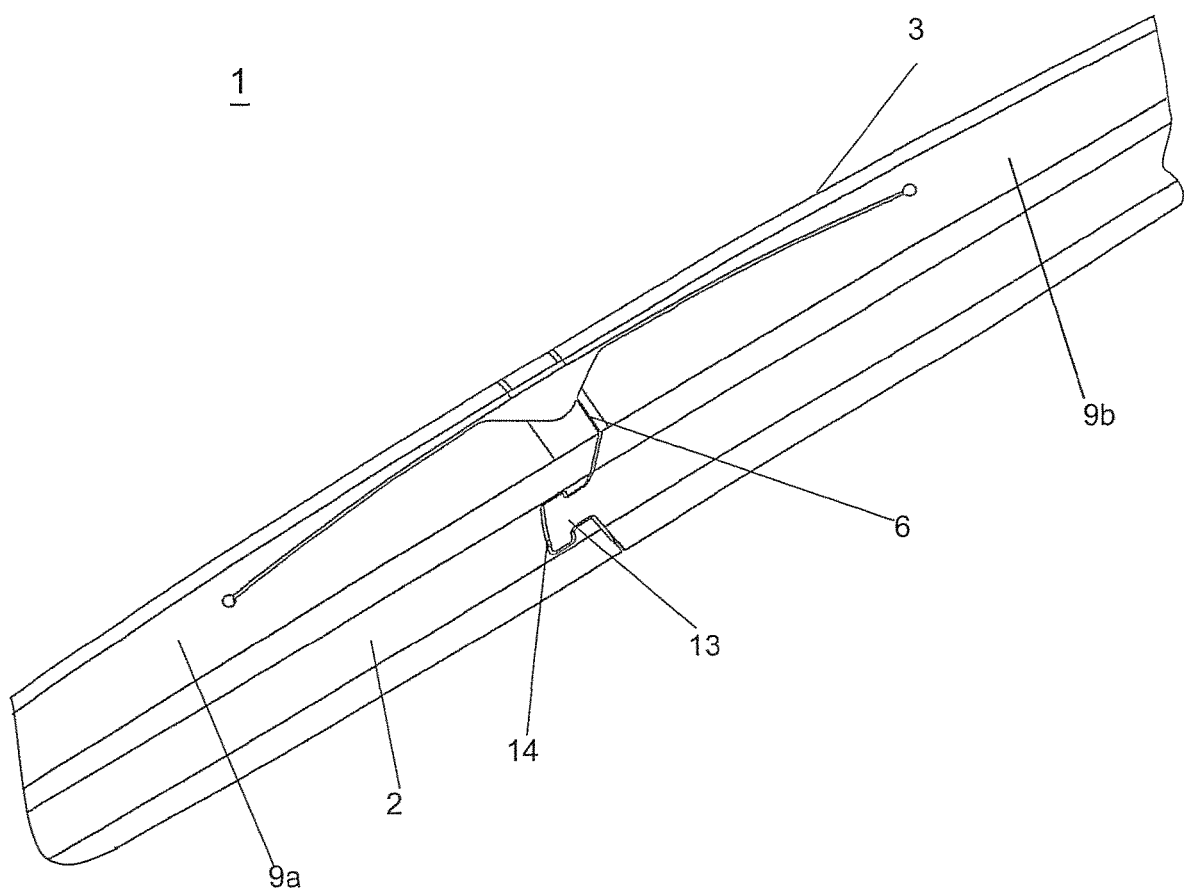
FIG. 4 illustrates a perspective view of another embodiment of the bone plate according to the invention.
Figure 5:
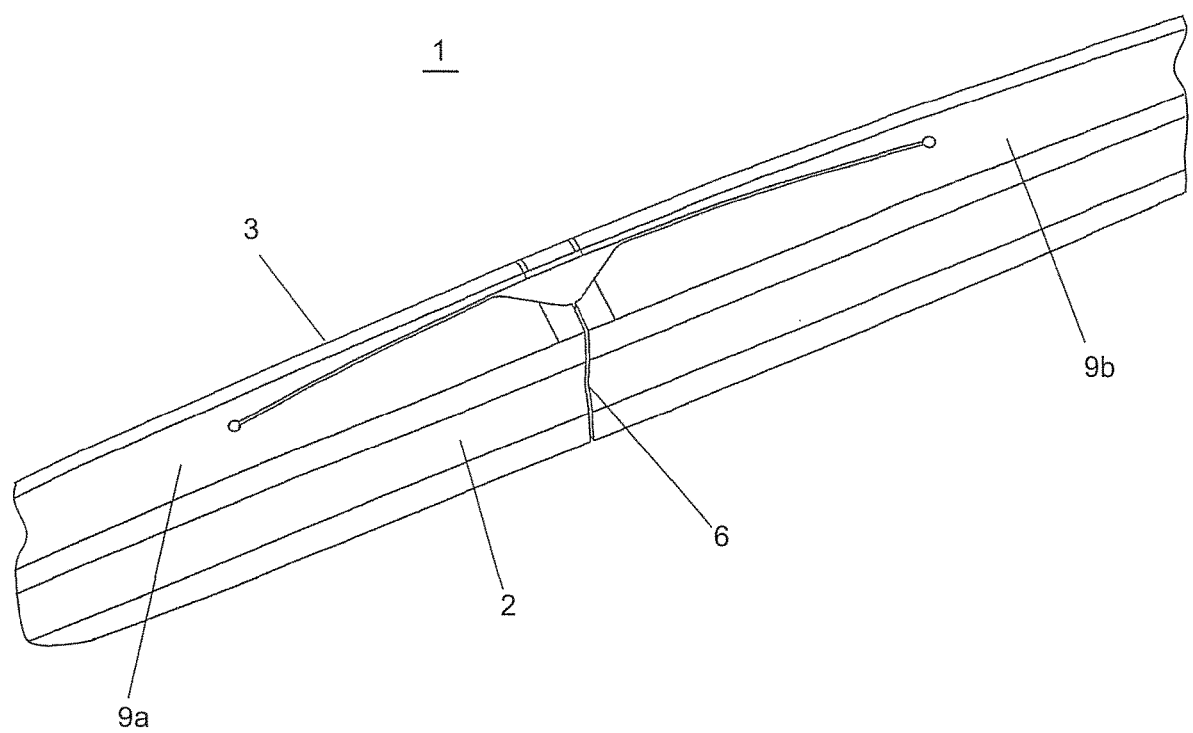
FIG. 5 illustrates a perspective view right up from below of a further embodiment of the bone plate according to the invention.
Figure 6:
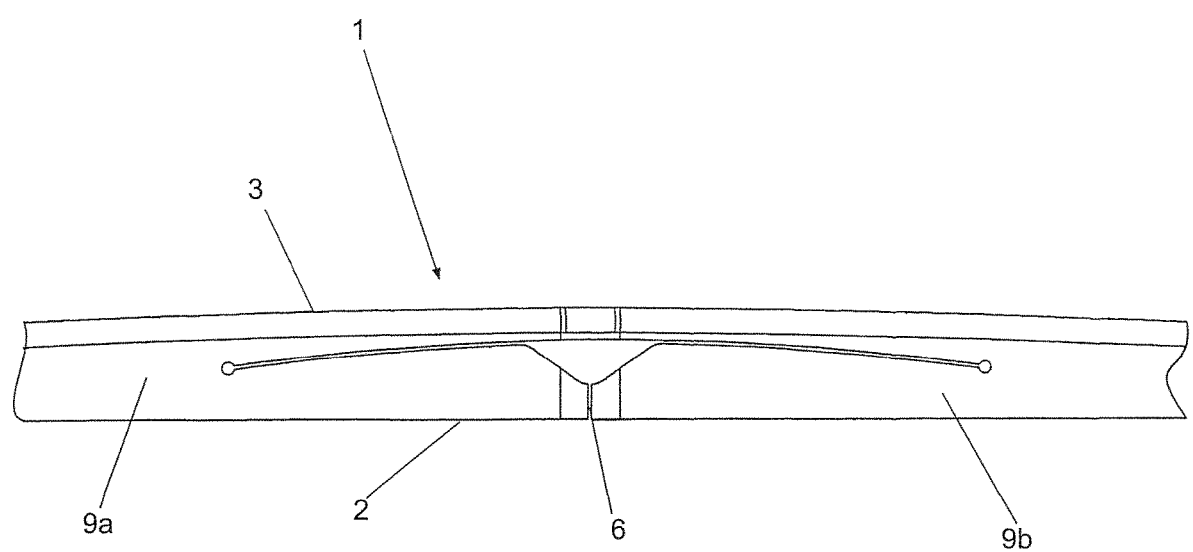
FIG. 6 illustrates a side view of a portion of the bone plate of FIG. 5.

FIG. 4 illustrates another embodiment of the bone plate 1 according to the invention wherein the slot 6 has three sections between the lower surface 2 and the upper surface 3 of the bone plate 1. A lower section extends from the lower surface 2 towards the upper surface 2, vertically adjacent thereto a central section is arranged and an upper section extends from the central section towards the upper surface 3 of the bone plate 1. In the lower section the slot 6 extends across the bone plate 1 along the form of an Ω in a view on the lower surface 2 of the bone plate 1. In this lower section the slot 6 forms a nose 13 which protrudes from one of the rigid sections 9b of the bone plate 1 along the longitudinal axis 4 and which has an enlarged free end. The adjoining end of the other rigid section 9a of the bone plate 1 is concavely formed so as to form an encompassment 14 that receives the nose 13 in such a way that movement of the nose 13 relative to the encompassment 14 is limited in both directions along the longitudinal axis 4 of the bone plate 1. In the undeformed state of the bone plate 1 the slot 6 extends between the nose 13 and the encompassment 14 with the width W measured at the lower surface 2. The encompassment 14 encloses the nose 13 more than 180° in a view on the lower surface 2 so that bending of the bridging portion 7 is limited in both directions, i.e. in a first direction where the maximum tensile forces occur on the upper surface 3 and in a second direction where the maximum compressive forces occur on the upper surface 3 so as to provide resistance against tensile forces and valgus bending. The central section has a constant cross-section across the bone plate 1, wherein the width measured in a longitudinal section of the bone plate 1 increases towards the upper section. The upper section of the slot 6 extends in the direction of the longitudinal axis 4 of the bone plate 1 and forms two curved horizontal legs. Similarly to the "T" shaped slot 6 of FIG. 14 the two legs extend in the direction of the longitudinal axis 4 of the bone plate 1 to a maximum extension E of the width of the slot 6 measured parallel to the longitudinal axis 4.

FIGS. 5 to 9 illustrate a further embodiment of the bone plate 1 according to the invention wherein similarly to the embodiment of FIG. 4 the slot 6 has three sections between the lower surface 2 and the upper surface 3 of the bone plate 1. A lower section extends from the lower surface 2 towards the upper surface 2, vertically adjacent thereto a central section is arranged and an upper section extends from the central section towards the upper surface 3 of the bone plate 1. The configuration of the slot 6 differs from the slot 6 of FIG. 4 only therein that the lower section the slot 6 linearly extends across the bone plate 1 in a view on the lower surface 2 of the bone plate 1.

Figure 7:
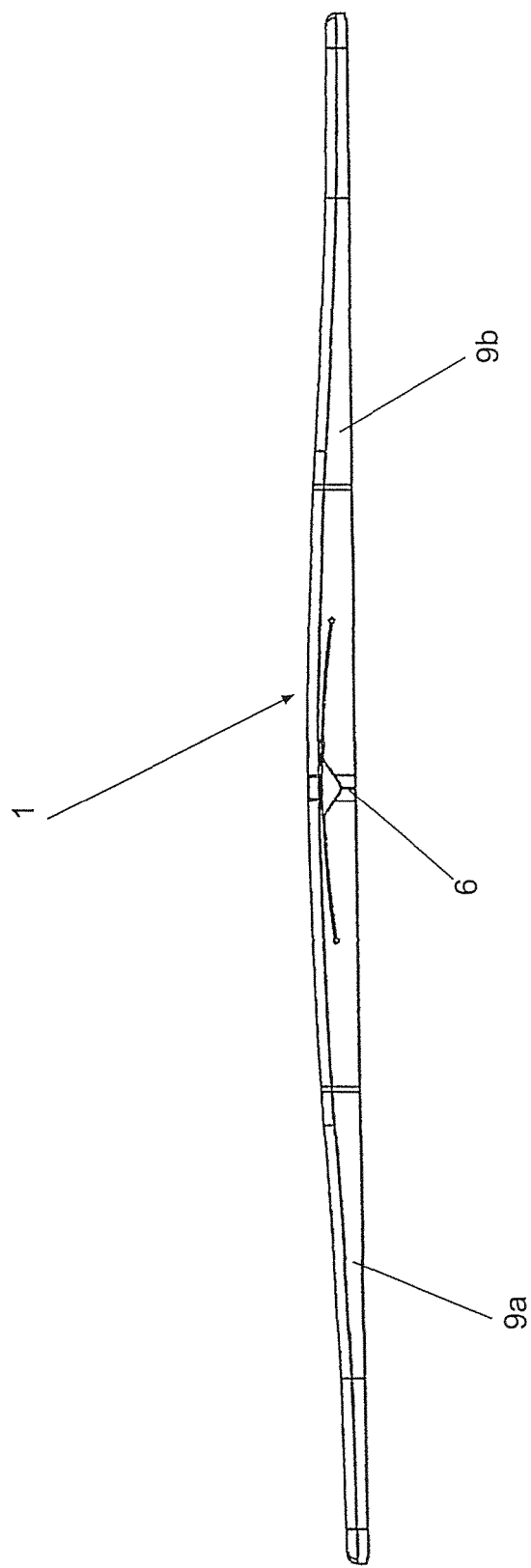
FIG. 7 illustrates a side view of the complete bone plate of FIG. 5.
Figure 8:
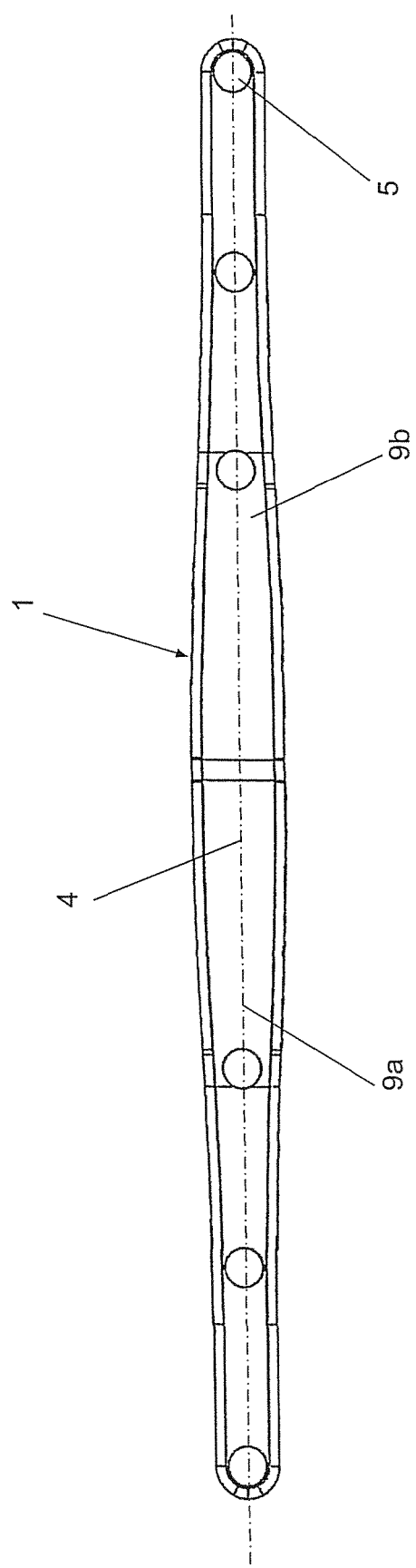
FIG. 8 illustrates a top view of the bone plate of FIG. 5.
Figure 9:
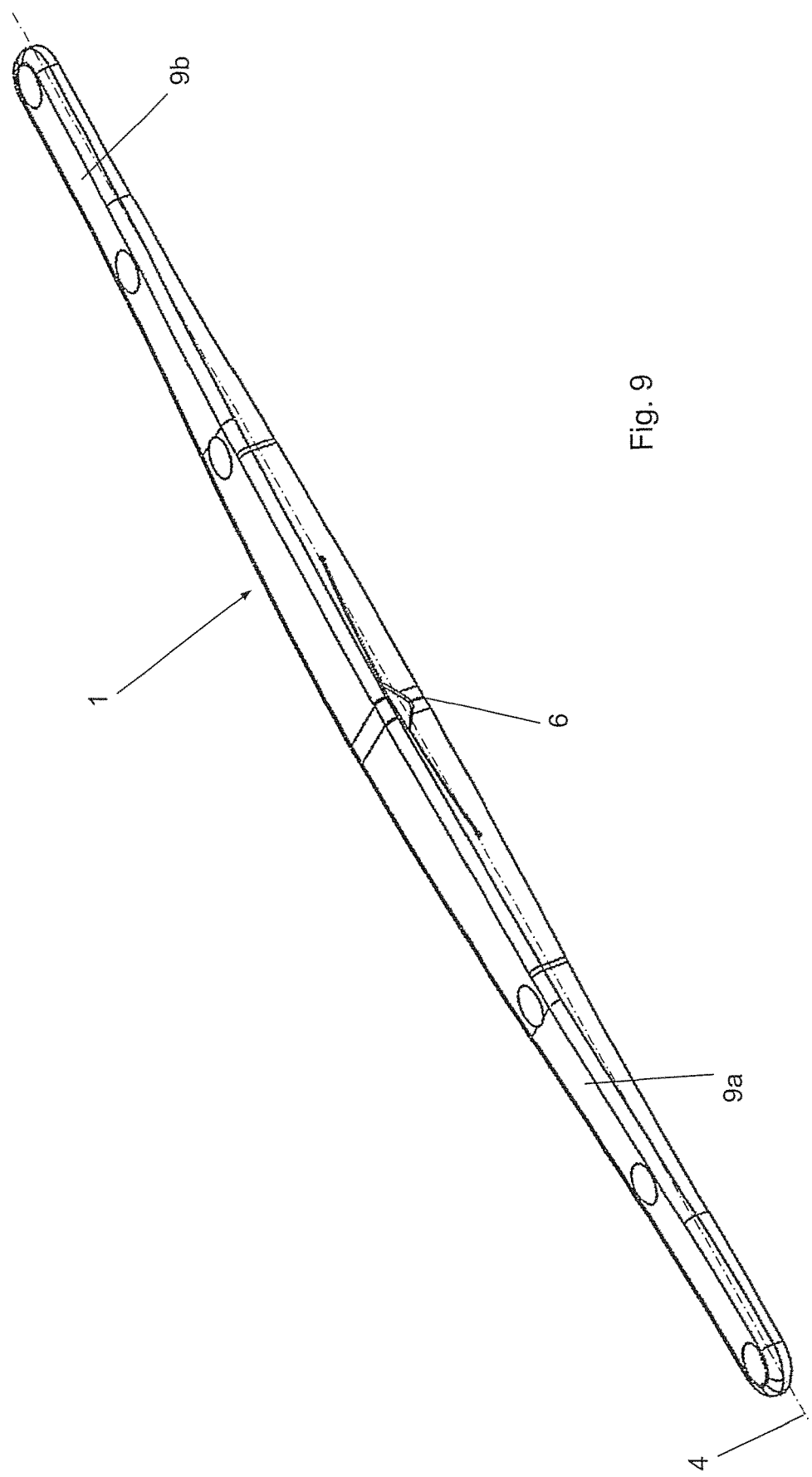
FIG. 9 illustrates a perspective view right up from below of a portion of the bone plate of FIG. 5.

As best seen in FIGS. 7 and 8 the thickness of the bone plate 1 and the plate width gradually decrease from the slot 6 towards the ends of the bone plate 1. Suitable dimensions of the bone plate 1 are, exemplarily (but not limited), a thickness in the range of 6 mm-12 mm and a width measured at the lower surface 2 and orthogonally to the longitudinal axis 4 in the range of 14 m-22 mm. For an application of the bone plate 1 on the femur the thickness is preferably in the range of 8 mm-10 mm and typically amounts to 9 mm.

The plate holes 5 can be configured as variable angle holes. Alternatively, one or more of the plate holes 5 can be configured to receive an angular stable locking screw at a predefined angle. For this purpose the one or more plate holes 5 can be conical or can comprise a conical interior thread. Exemplarily but not limiting, the 3D-shape of the bone plate 1 is pre-shaped to a specific anatomical fit.

Furthermore, in an alternative embodiment the bone plate 1 can comprise two slots 6 which are spaced apart of more than 50 mm measured parallel to the longitudinal axis 4 of the bone plate 1.

Figure 10:
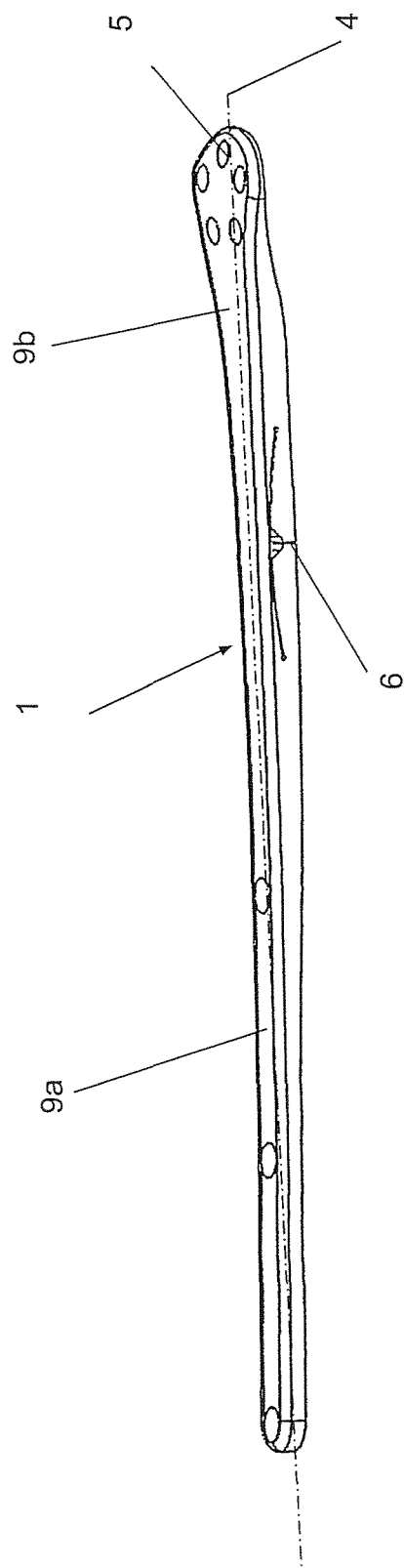
FIG. 10 illustrates a perspective view of a further embodiment of the bone plate according to the invention.

The embodiment of the bone plate 1 according to the invention illustrated in FIG. 10 is configured for an application on metaphyseal fractures, such as the distal femur, the proximal humerus or the distal/proximal tibia and differs from the embodiment of FIGS. 5 to 9 only therein that one rigid section 9b of the bone plate 1 is spoon-shaped and that the slot 6 is arranged closer to the spoon-shaped rigid section 9b. Further, the plate holes 5 in the spoon-shaped rigid section 9b are arranged in the enlarged portion which is terminally arranged on the bone plate 1 while the plate holes 5 in the other rigid section 9a are arranged along the longitudinal axis 4 of the bone plate 1 and evenly spaced from each other. For the specific application of the bone plate 1 on the humerus or tibia the thickness is in the range of 4 mm-7 mm and amounts typically to 6 mm.

Figure 11:
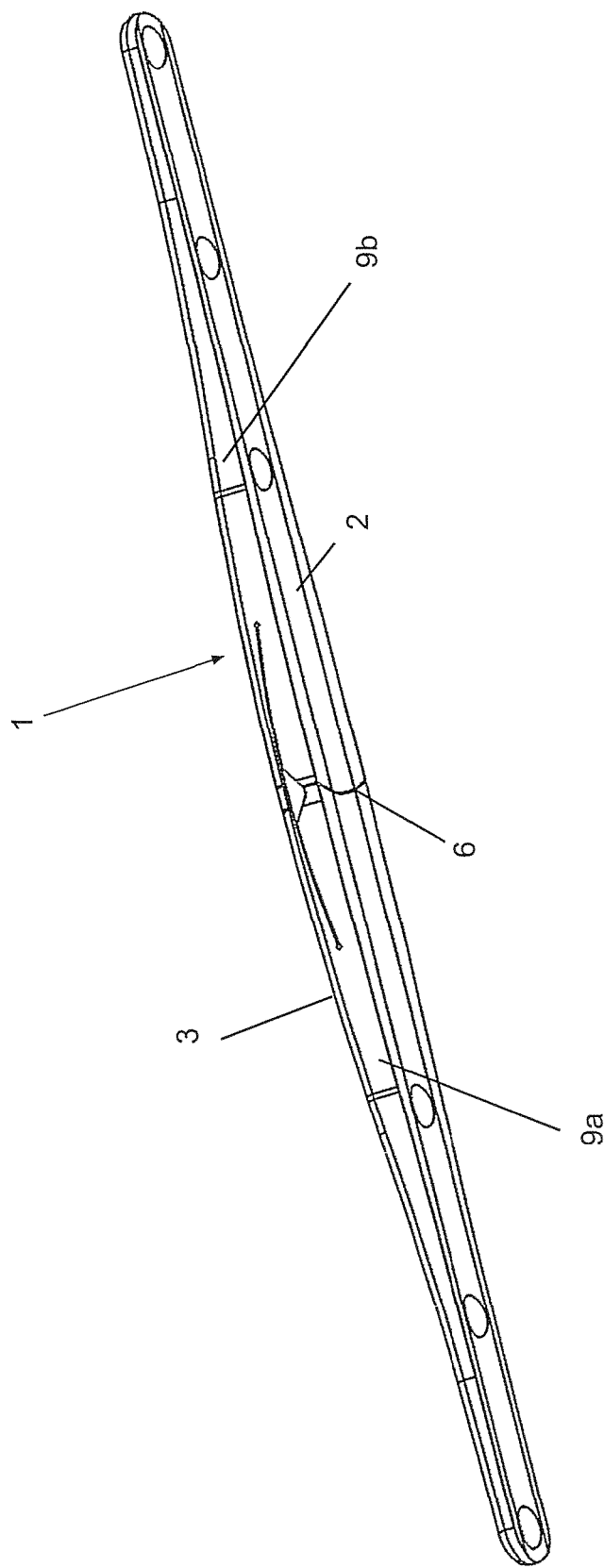
FIG. 11 illustrates a perspective view right up from below of again a further embodiment of the bone plate according to the invention.

FIG. 11 illustrates a further embodiment of the bone plate 1 according to the invention which differs from the embodiment of FIGS. 5-9 only therein that the slot 6 curvedly extends across the bone plate 1 in a view on the lower surface 2 of the bone plate 1 so that once the slot 1 is closed the bone plate 1 the torsional rigidity of the bone plate 1 is significantly increased.

Figure 12:
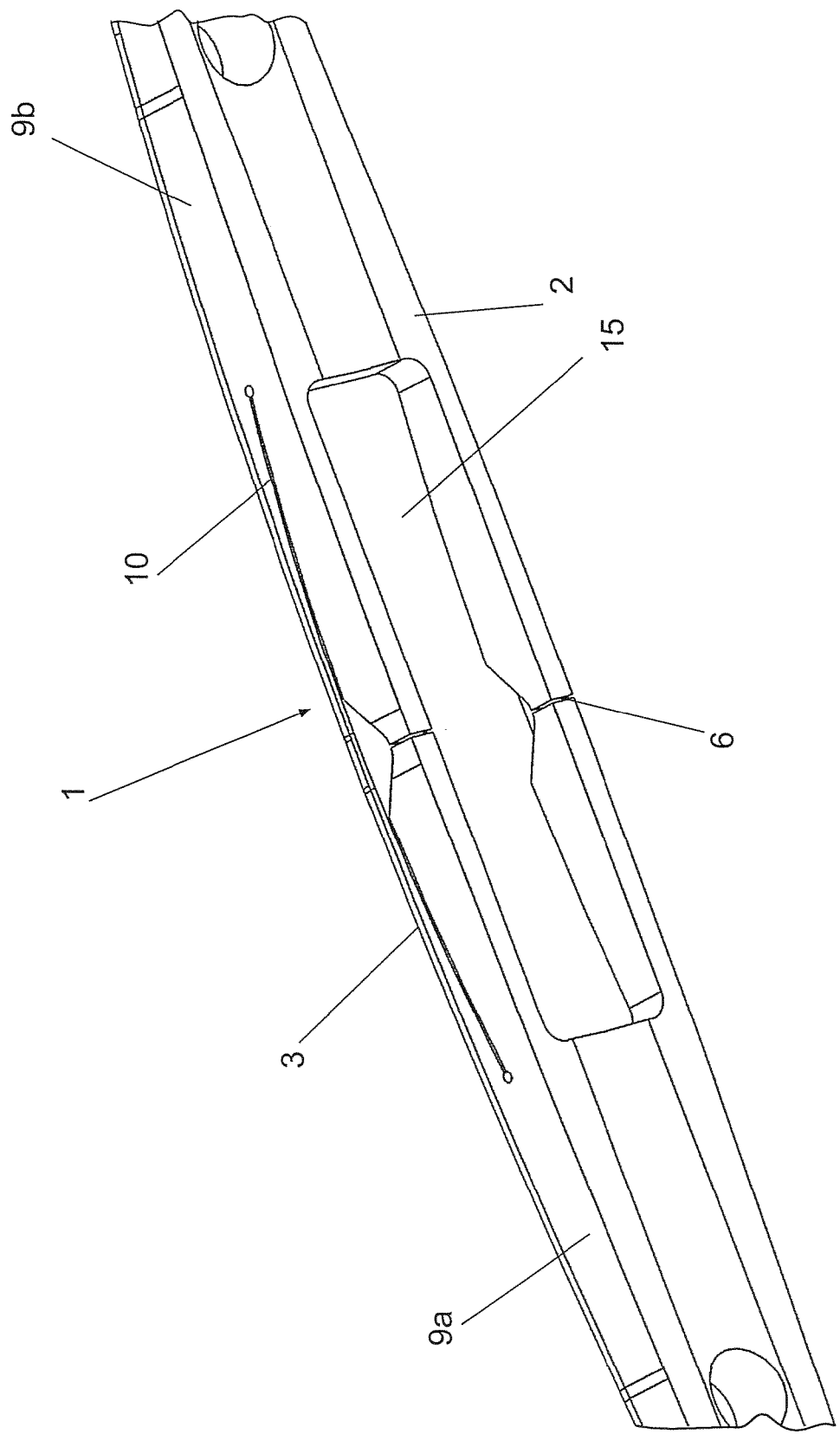
FIG. 12 illustrates a perspective view right up from below of again another embodiment of the bone plate according to the invention.

Again a further embodiment of the bone plate 1 according to the invention is illustrated in FIG. 12 wherein this embodiment differs from the embodiment of FIGS. 5-9 only therein that the flexible section 10 of the bone plate 1 comprises a compartment 15 extending from the lower surface 2 towards the upper surface 3. The compartment 15 is open at the lower surface 2 of the bone plate 1 and formed by two longitudinal nose pieces extending from each rigid section 9a, 9b towards the slot 6 which is arranged between the adjoining end faces of each pair of longitudinally opposing nose-pieces. The compartment 15 is suitable to accommodate one or more sensors (not shown), preferably for measuring strain, displacement, load or pressure or temperature. Alternatively or additionally the compartment 15 is suitable to accommodate one or more actuators, to alter the implant's mechanical properties, or store drugs for controlled release or to provide space for callus growth.

Figure 13:
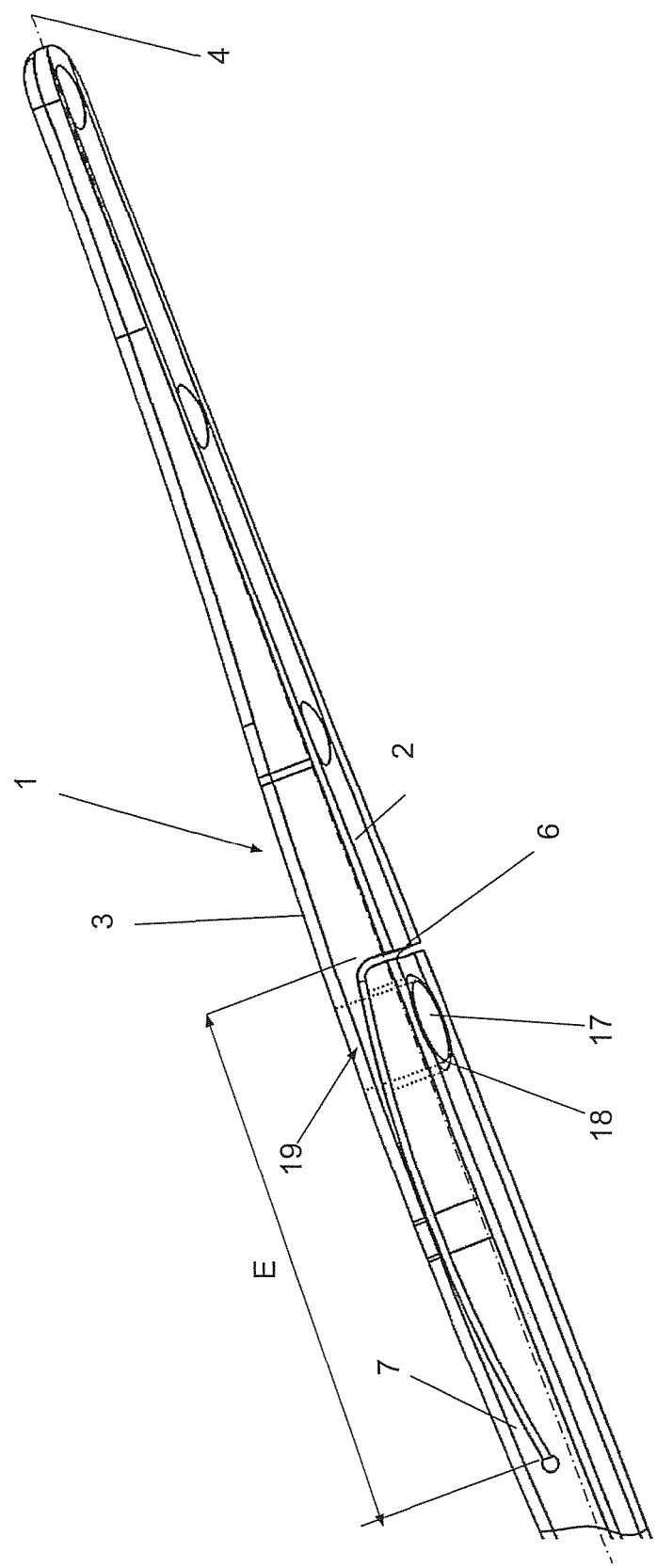
FIG. 13 illustrates a perspective view right up from below of a further embodiment of the bone plate according to the invention.

FIG. 13 shows an embodiment of the bone plate 1 according to the invention which comprises a cylindrical bolt 16 rigidly connected to the bridging portion 7 of the bone plate 1. The slot 6 has an L-shape similar to FIG. 15b. The free end of the shorter leg of the "L" opens into the lower surface 2 with a width W and the longer leg of the "L" extends curvedly in the direction of the longitudinal axis 4 and provides the maximum extension E of the width of the slot 6. The extension of the slot 6 in the longitudinal direction permits to reduce the bending resistance of the bone plate 1 under low loading magnitudes. The bolt 16 extends to the lower surface 2 of the bone plate 1 and crosses the longer leg of the L-shaped slot 6. Below the horizontal longer leg of the L-shaped slot 6 a longitudinal nose-piece extends from the rigid section 9a towards the slot 6, wherein this nose-piece comprises a cavity 17 which extends from the lower surface 2 of the bone plate 1 towards the upper surface 3 and which runs into the horizontal longer leg of the L-shaped slot 6. The cavity 17 is, exemplarily but not limiting, configured as a bore hole having a diameter larger than the bolt 16 so that the bolt 16—in the undeformed state of the bone plate 1—is concentrically positioned in the cavity 17 with a clearance C. Under bending of the bone plate 1, the bolt 16 acts as limiter of the plate deflection when contact between the bolt 16 and the cavity 17, i.e. the bore hole is achieved. Thus, similar to the embodiment of FIG. 4 bending of the bridging portion 7 is limited in both directions, i.e. in a first direction where the maximum tensile forces occur on the upper surface 3 and in a second direction where the maximum compressive forces occur on the upper surface 3 so as to provide resistance against valgus bending as well. Furthermore, the bolt/cavity configuration provides a loose-lock stability at the bone fracture, which is beneficial for bone healing. The bolt 16 forms a material section 18 which is rigidly connected to the bridging portion 7 which forms an upper section of the bone plate 1 adjacent to the upper surface 3 of the bone plate 1.

Figure 16:
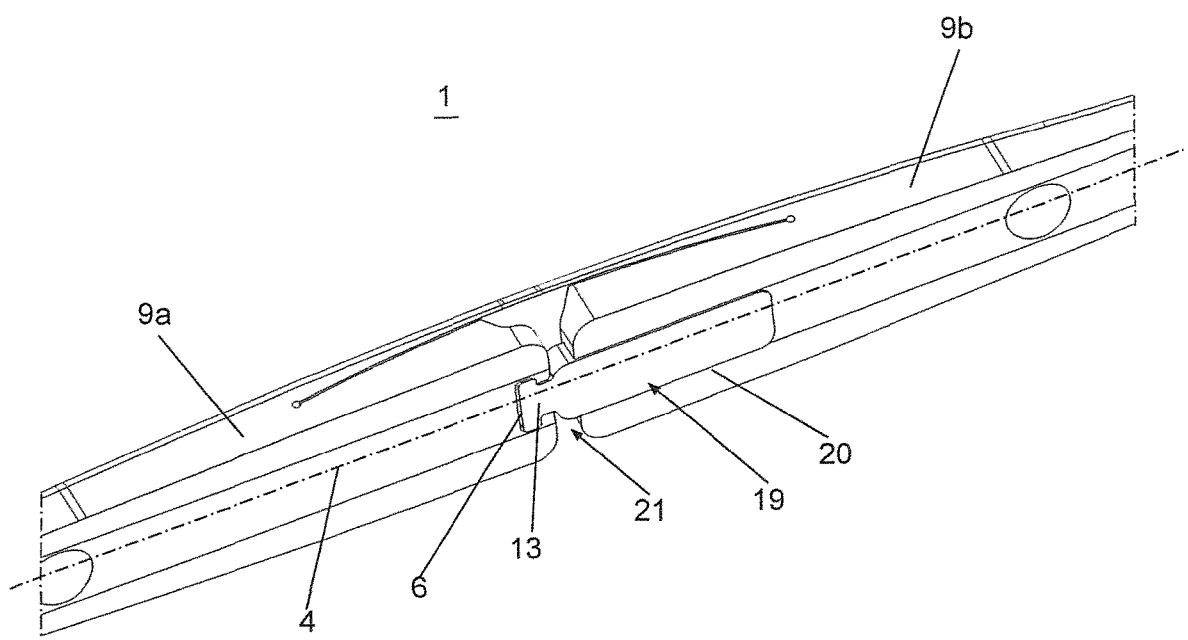
FIG. 16 illustrates a perspective view of again another embodiment of the bone plate according to the invention.

FIG. 16 illustrates another embodiment of the bone plate 1 according to the invention which differs from the embodiment of FIG. 4 only therein that the nose 13 which protrudes from one of the rigid sections 9b of the bone plate 1 along the longitudinal axis 4 is configured as an insert 19 which is introduced in a recess 20 in the respective rigid section 9b and affixed to the bone plate 1. The embodiment of the bone plate 1 of FIG. 16 is therefore realized from two separate parts. Furthermore, a gap 21 can be formed between the two rigid sections 9a,9b in the range of the lower section of the slot 6 which has a gap width that is larger than the width of the slot 6.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The invention claimed is:

1. A bone plate comprising a lower surface, an upper surface, a thickness T measured between the lower surface and the upper surface, a longitudinal axis, a plurality of plate holes running from the lower surface to the upper surface, and a slot extending from the lower surface towards the upper surface, wherein:
   the slot has a width W measured at the lower surface parallel to the longitudinal axis that is greater than 0 when the bone plate is unbent;
   the slot extends to a maximum distance D measured from the lower surface towards the upper surface of 0.4-0.9 times the thickness T of the bone plate;
   the slot has a maximum width E also measured parallel to the longitudinal axis that is at least 0.8 mm when the bone plate is unbent;
   the slot allows the bone plate to bend longitudinally by an additional amount as compared to a bone plate that is identical but which is unslotted, the additional amount being no greater than 20°; and
   a length of the lower surface is shortened by at most 1 mm upon closure of the slot at the lower surface of the bone plate by bending the bone plate such that the width W is equal to 0.

2. The plate according to claim 1, wherein the width W is in a range of 0.1 to 1.3 mm when the bone plate is unbent.

3. The bone plate according to claim 1, further comprising a material section rigidly connected to an upper section of the bone plate adjacent to the upper surface that extends to the lower surface and thereby crosses the slot, the material section sitting inside a cavity extending from the lower surface towards the upper surface and having a clearance C.

4. The plate according to claim 3, wherein the material section is a bolt.

5. The bone plate according to claim 1, wherein the width W of the slot is larger than 0.20 mm when the bone plate is unbent.

6. The bone plate according to claim 1, wherein the width W of the slot is smaller than 0.35 mm when the bone plate is unbent.

7. The bone plate according to claim 1, wherein the maximum distance D is at least 2 mm.

8. The bone plate according to claim 1, wherein the lower surface is a bone-contacting surface.

9. The bone plate according to claim 1, wherein the thickness T is in a range of 6 mm-12 mm.

10. The bone plate according to claim 1, wherein the thickness T in a range of 8 mm-10 mm.

11. The bone plate according to claim 1, wherein the thickness T is in a range of 4 mm-7 mm.

12. The bone plate according to claim 1, wherein the bone plate has a width measured at the lower surface at a position of the slot perpendicular to the longitudinal axis in a range of 14 mm-22 mm.

13. The bone plate according to claim 1, wherein the additional amount is at least 1.0°.

14. The bone plate according to claim 1, wherein the additional amount is at most 5°.

15. The bone plate according to claim 1, wherein the bone plate is configured such that a force in a range of 50-400 N acting essentially parallel to the longitudinal axis of the bone plate with an offset of 10 mm to 30 mm from the lower surface of the bone plate is sufficient to close the slot at the lower surface of the bone plate by bending the bone plate such that the width W is equal to 0.

16. The bone plate according to claim 1, wherein the slot has a shape of an "L", a free end of a shorter leg of the "L" opens into the lower surface and has the width W greater than 0 when the bone plate is unbent, a longer end of the "L" runs essentially parallel to the longitudinal axis, and the maximum width E is measured through the longer end of the "L".

17. The bone plate according to claim 1, wherein the slot has a shape of a "T", a free end of a vertical leg of the "T" opens into the lower surface and has the width W greater than 0 when the bone plate is unbent, two horizontal legs of the "T" run essentially parallel to the longitudinal axis, and the maximum width E is measured through the two horizontal legs of the "T".

18. The bone plate according to claim 1, wherein the slot has a curved-shaped form as viewed in a longitudinal cross-section of the bone plate, the curved-shaped enlarging from the lower surface towards the upper surface.

19. The bone plate according to claim 1, wherein the slot has an Ω-shaped form as viewed on the lower surface of the bone plate, and wherein the Ω-shaped form has an axis of symmetry extending in a direction of the longitudinal axis of the bone plate.

20. The bone plate according to claim 1, wherein the slot has
   (i) a lower part essentially running in a direction of the thickness of the bone plate and which opens into the lower surface; and
   (ii) an upper part essentially running parallel to the longitudinal axis and which is closed with respect to the upper surface.

21. The bone plate according to claim 1, wherein the bone plate has a width measured at the lower surface at a position of the slot perpendicular to the longitudinal axis, and wherein the thickness T of the bone plate and the width of the bone plate gradually decrease from the slot towards both ends of the bone plate.

22. The bone plate according to claim 1, wherein at least one of the plurality of plate holes is configured to receive an angular stable locking screw at a predefined angle.

23. The bone plate according to claim 1, wherein at least one of the plurality of plate holes is configured to receive a variable angle locking screw.

24. The bone plate according to claim 1, wherein the plurality of plate holes have different sizes to receive bone screws of different diameters.

25. The bone plate according to claim 1, wherein the bone plate has a 3D-shape that is pre-shaped to a specific anatomical fit.

26. The bone plate according to claim 1, wherein the bone plate has two slots that are spaced apart a distance from each other measured longitudinally of more than 50 mm.

27. The bone plate according to claim 1, wherein the bone plate has a compartment extending from the lower surface towards the upper surface to accommodate one or more sensors.

28. The bone plate according to claim 1, wherein the bone plate has a compartment extending from the lower surface towards the upper surface to accommodate one or more actuators for storing drugs for controlled release or for providing space for callus growth.

29. The bone plate according to claim 2, wherein the width W of the slot when the bone plate is unbent is essentially equal to the maximum width E of the slot.

30. The bone plate according to claim 1, wherein the bone plate is configured in two-piece form.

31. The bone plate according to claim 1, wherein the bone plate is made of stainless steel, titanium or a titanium alloy.

32. The bone plate according to claim 1, wherein the bone plate is configured for treating bone fractures.

33. A method of manufacture of a bone plate according to claim 1, comprising producing the slot by cavity sinking EDM.

\* \* \* \* \*